US009628723B2

(12) United States Patent
Yu et al.

(10) Patent No.: US 9,628,723 B2
(45) Date of Patent: Apr. 18, 2017

(54) COMPUTED TOMOGRAPHY SCANNER CALIBRATION WITH ANGLE CORRECTION FOR SCAN ANGLE OFFSET

(71) Applicant: TOSHIBA MEDICAL SYSTEMS CORPORATION, Otawara-shi (JP)

(72) Inventors: Zhou Yu, Palatine, IL (US); Yu Zou, Naperville, IL (US); Yuexing Zhang, Naperville, IL (US); Xiaolan Wang, Buffalo Grove, IL (US)

(73) Assignee: TOSHIBA MEDICAL SYSTEMS CORPORATION, Otawara-shi (JP)

(*) Notice: Subject to any disclaimer, the term of this patent is extended or adjusted under 35 U.S.C. 154(b) by 107 days.

(21) Appl. No.: 14/622,372

(22) Filed: Feb. 13, 2015

(65) Prior Publication Data
US 2016/0239971 A1    Aug. 18, 2016

(51) Int. Cl.
*H04N 5/32*    (2006.01)
*A61B 6/03*    (2006.01)
(Continued)

(52) U.S. Cl.
CPC ............... *H04N 5/32* (2013.01); *A61B 6/032* (2013.01); *A61B 6/4241* (2013.01); *A61B 6/4266* (2013.01); *A61B 6/5211* (2013.01); *A61B 6/582* (2013.01); *G06T 11/005* (2013.01); *A61B 6/488* (2013.01); *A61B 6/583* (2013.01)

(58) Field of Classification Search
CPC . A61B 2560/0223; A61B 6/032; A61B 6/583; A61B 6/582; A61B 6/584; A61B 6/585; A61B 6/5211; A61B 6/4241; A61B 6/4266; G06T 7/0038; G06T 11/005; G06T 11/006; G06T 2211/421; G01N 23/046; G01N 2223/303; G01T 7/005; H04N 5/32
See application file for complete search history.

(56) References Cited

U.S. PATENT DOCUMENTS

| | | | |
|---|---|---|---|
| 2010/0272342 A1* | 10/2010 | Berman | A61B 6/032 382/131 |
| 2013/0114799 A1* | 5/2013 | Yamakawa | A61B 6/14 378/207 |
| 2016/0023019 A1* | 1/2016 | Filiberti | A61N 5/1075 600/1 |

FOREIGN PATENT DOCUMENTS

JP    2013-192950 A    9/2013

* cited by examiner

*Primary Examiner* — Vu Le
*Assistant Examiner* — Kenny Cese
(74) *Attorney, Agent, or Firm* — Oblon, McClelland, Maier & Neustadt, L.L.P.

(57) ABSTRACT

A method and apparatus of aligning calibration projection data with object projection data to improve calibration corrections of the object projection data. In a first implementation, the method interpolates and upsamples both the calibration and object data, then shifts the upsampled calibration data to match a sub-view angular offset of the object data, and then performs calibration corrections before downsampling the corrected object data. In a second implementation, the method continuously scans an object space—with the object absent (present) in the object space—to obtain calibration data (object absent) and object data (object present) both having the same sub-view angular offset. In a third implementation, the method obtains multiple scans having different sub-view angular offsets, organizes the scans into bins according to their respective sub-view angular offsets, and chooses the appropriate sub-view angular offsets bin for calibration corrections of the object data.

20 Claims, 7 Drawing Sheets

(51) Int. Cl.
*A61B 6/00* (2006.01)
*G06T 11/00* (2006.01)

COMPUTED TOMOGRAPHY SCANNER CALIBRATION WITH ANGLE CORRECTION FOR SCAN ANGLE OFFSET

BACKGROUND

Field

Embodiments described herein relate generally to calibrating and correcting projection data, and more specifically to matching the offset angle of the object projection data with the offset angle of calibration data, and then performing corrections to the object projection data using the calibration data.

Description of the Related Art

Computed tomography (CT) systems and methods are widely used, particularly for medical imaging and diagnosis. CT systems generally create images of one or more sectional slices through a subject's body. A radiation source, such as an X-ray source, irradiates the body from one side. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body substantially in the plane of the slice. The attenuation of the radiation that has passed through the body is measured by processing electrical signals received from the detector.

FIG. 1A shows a CT sinogram, which is a plot of attenuation through the body as a function of "space" along a detector array (horizontal) and "time/angle" of a scan of measurements performed at a series of projection angles (vertical). The space dimension refers to the position along a one-dimensional array of X-ray detectors. The time/angle dimension refers to the projection angle of X-rays changing as a function of time, such that as time progresses the projection angle increments and projection measurements are performed at a linear succession of projection angles. The attenuation resulting from a particular volume (e.g., a vertebra) will trace out a sine wave around the vertical axis—volumes farther from the axis of rotation having sine waves with larger amplitudes, the phase of a sine wave determining the volume's angular position around the rotation axis. Performing an inverse Radon transform or equivalent image reconstruction method reconstructs an image from the projection data in the sinogram—the reconstructed image corresponding to a cross-sectional slice of the body, as shown in FIG. 1A.

Conventionally, energy-integrating detectors have been used to measure CT projection data. Now, recent technological developments are making photon-counting detectors a feasible alternative to conventional energy-integrating detectors. Photon-counting detectors have many advantages, including their capacity for performing spectral CT. To obtain the spectral nature of the transmitted X-ray data, the photon-counting detectors split the X-ray beam into its component energies or spectrum bins and count a number of photons in each of the bins. Since spectral CT involves the detection of transmitted X-rays at two or more energy levels, spectral CT generally includes dual-energy CT by definition.

Many clinical applications can benefit from spectral CT technology, which can provide improvement in material differentiation and beam hardening correction. Further, semiconductor-based photon-counting detectors are a promising candidate for spectral CT, which is capable of providing better spectral information compared with conventional spectral CT technology (e.g., dual-source, kVp-switching, etc.).

One advantage of spectral CT, and spectral X-ray imaging in general, is that materials having atoms with different atomic number Z also have different spectral profiles for attenuation. Thus, by measuring the attenuation at multiple X-ray energies, materials can be distinguished and the attenuation can be attributed to a particular atom (i.e., effective Z). This attribution enables spectral projection data to be mapped from the spectral domain to the material domain using a material decomposition. In some instances, this material decomposition is performed using a dual-energy analysis method.

The dual-energy analysis method can be used because the attenuation of X-rays in biological materials is dominated by two physical processes (i.e., photoelectric scattering and Compton scattering). Thus, the attenuation coefficient as a function of energy can be approximated by the decomposition $$\mu(E,x,y)=\mu_{PE}(E,x,y)+\mu_C(E,x,y),$$

wherein $\mu_{PE}(E, x, y)$ is the photoelectric attenuation and $\mu_C(E, x, y)$ is the Compton attenuation. This attenuation coefficient can be rearranged instead into a decomposition of a high-Z material (i.e., material 1) and a low-Z material (i.e., material 2) to become $$\mu(E,x,y)\approx\mu_1(E)c_1(x,y)+\mu_2(E)c_2(x,y),$$

wherein $c_{1,2}(x,y)$ is a spatial function describing how much the imaged object located at position (x,y) is represented by material 1 and material 2, respectively.

In some CT systems, including those having topologies with a ring of photon-counting detectors inside the circular path of the X-ray source, measurement artifacts will be calibrated out using calibration scans similar to the object scans that collect projection data of the image object. For best results, any angular offset between the calibration scans and the object scans should be corrected. Correcting the angular offset will improve image quality of the reconstructed image. The angular offset between the calibration scans and the object scans can be described as a difference between the sub-view angular offset of the calibration projection data and the sub-view angular offset of the object projection data. The "sub-view angular offset" of projection data—where "projection data" refers to a collection of projection measurements for a series of projection angles—is defined for a given scan as the average offset angle between the actual projection angles and the nominal projection angle recorded using the data acquisition and motion control systems of the CT scanner. This difference between actual and nominal angles can arise from the tolerance limitations in real-world measurement systems (e.g., backlash in the gears and resolution limitations of the measurement encoders).

Generally, the sub-view angular offset will be different for different scans, where "different scans" includes that the rotation of the CT system is stopped and restarted between scans. Because the calibration projection data will likely have a different sub-view angular offset than the object projection data, without correcting for the differences in sub-view angular offset residual measurement artifacts remain after calibration corrections, resulting in poorer image quality for reconstructed images. On the other hand, a method that matches sub-view angular offset of the object projection data and calibration projection data results in better cancellation of measurement artifacts in the calibration corrected projection data and improved image quality for reconstructed images from the corrected projection data.

BRIEF DESCRIPTION OF THE DRAWINGS

A more complete understanding of this disclosure is provided by reference to the following detailed description when considered in connection with the accompanying drawings, wherein.

DETAILED DESCRIPTION

Embodiments described herein relate generally to calibrating and correcting projection data, and more specifically to matching the offset angle of the object projection data with the offset angle of calibration data, and then performing corrections to the object projection data using the calibration data.

According to one embodiment, there is provided an apparatus comprising processing circuitry configured to obtain object projection data and calibration projection data, wherein the object projection data represents an intensity of x-rays transmitted through an image object and detected by x-ray detectors, the object projection data being measured at a plurality of projection angles relative to the image object, and the calibration projection data represents an intensity of x-rays transmitted through a predetermined calibration object and detected by x-ray detectors, the object projection data being measured at a plurality of projection angles relative to the calibration object. The processing circuitry is also configured to align the projection angles of the calibration projection data to have a sub-view angular offset matching the sub-view angular offset of the object projection data. Moreover, the processing circuitry is configured to correct the object projection data using the calibration projection data.

The embodiment of the apparatus also includes a gantry having an aperture with an object space in the aperture, where the object space is an intersection between the aperture and a projection plane of the X-rays from the X-ray source. The gantry also has a rotational component provided around the object space that is rotatably connected to a stationary component of the gantry. Moreover, the gantry has an X-ray source fixedly connected to the rotation component and radiating X-rays into the object space.

According to another embodiment is provided a method that includes obtaining object projection data and calibration projection data. The object projection data represents an intensity of X-rays transmitted through an image object and detected by X-ray detectors, the object projection data being measured at a plurality of projection angles relative to the image object. The calibration projection data represents an intensity of X-rays transmitted through a predetermined calibration object and detected by X-ray detectors, the object projection data being measured at a plurality of projection angles relative to the calibration object. The method also includes aligning the projection angles of the calibration projection data to have a sub-view angular offset matching the sub-view angular offset of the object projection data. Moreover, the method includes correcting the object projection data using the calibration projection data.

Figure 1A:
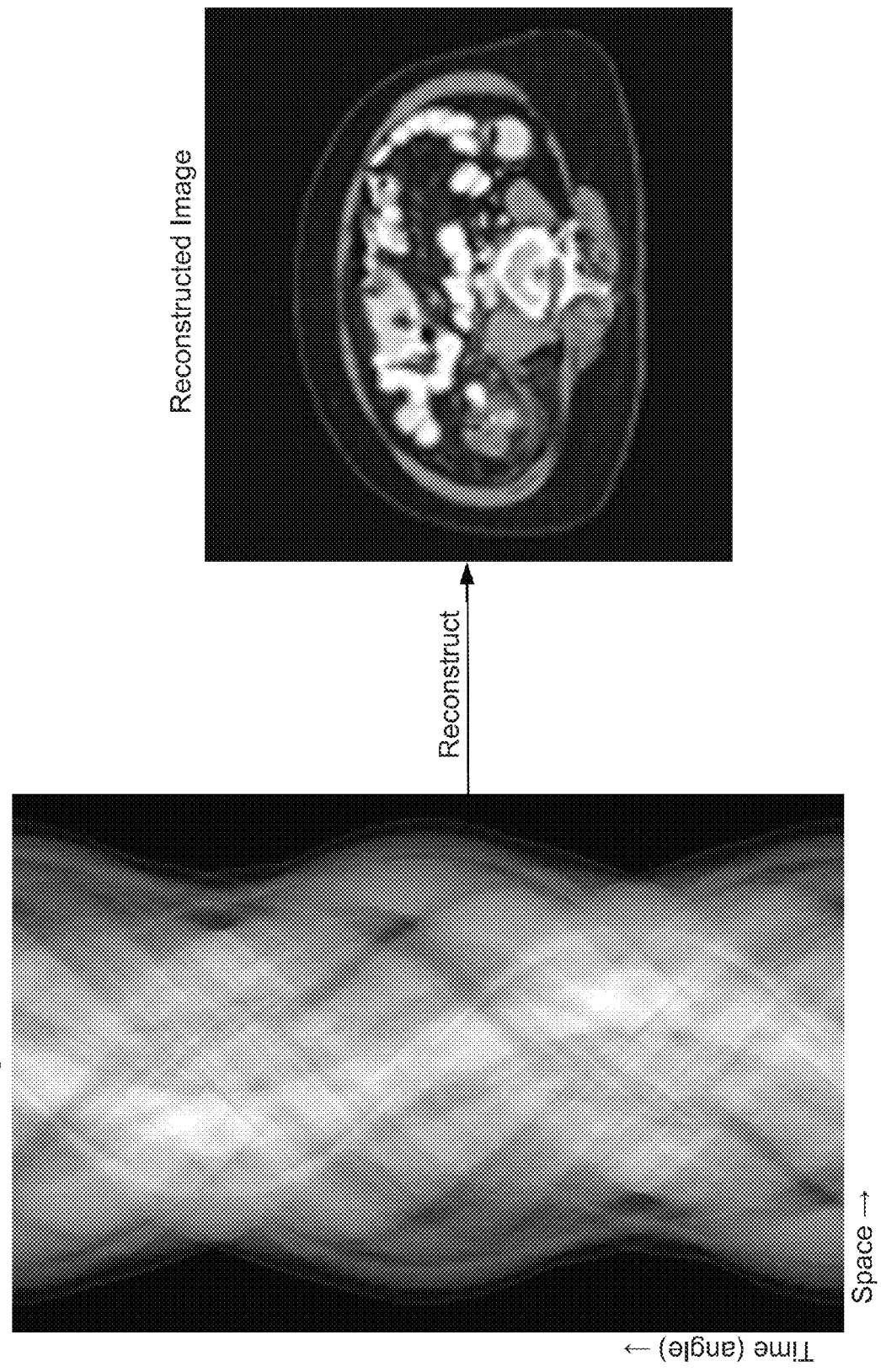
FIG. 1A shows a sinogram of projection data and a reconstructed image from the projection data, wherein the sinogram is plotted as a function of space (horizontal axis) and time/angle (vertical axis), and the reconstructed image is plotted with ventral/dorsal (vertical axis) and lateral (horizontal axis) dimensions, with attenuation plotted in shades of grey (more attenuation equals more white)
Figure 1B:
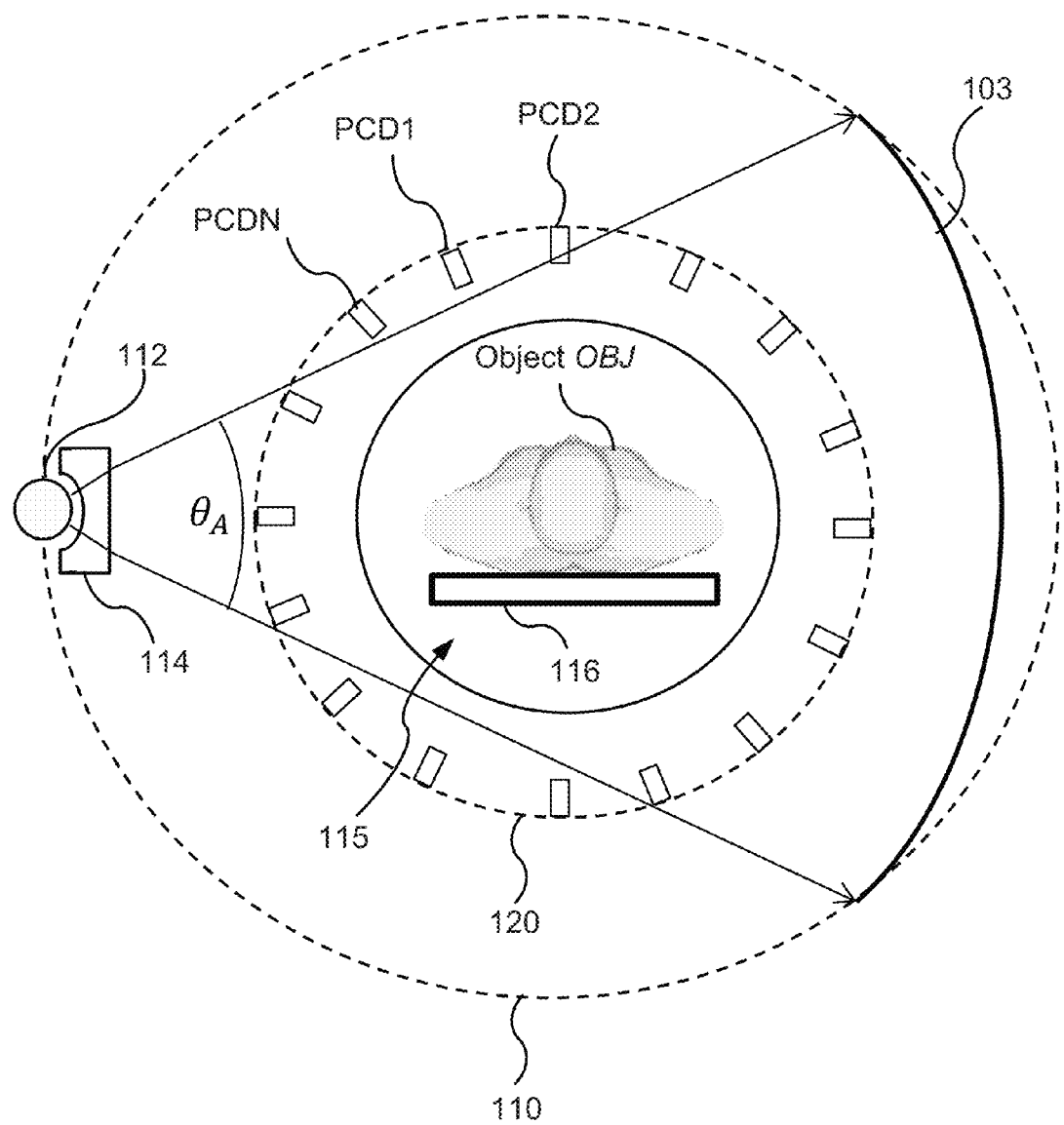
FIG. 1B shows a schematic of an implementation of an arrangement of X-ray source and X-ray detectors for a CT scanner.

Referring now to the drawings, wherein like reference numerals designate identical or corresponding parts throughout the several views, FIG. 1B shows source and detector portions of a computed tomography (CT) scanner having both energy-integrating detectors arranged in a third-generation geometry and photon-counting detectors arranged in a fourth-generation geometry. Illustrated in FIG. 1B is an implementation for placing the photon-counting detectors (PCDs) in a predetermined fourth-generation geometry in combination with a detector unit 103 in a predetermined third-generation geometry in a CT scanner system. The diagram illustrates relative positions among an object OBJ to be scanned resting on a table 116, an X-ray source 112, a collimator/filter 114, an X-ray detector 103, and photon-counting detectors PCD1 through PCDN. The PCDs have a front surface, oriented towards the object OBJ and a back surface oriented away from the object OBJ. X-rays traveling through the object OBJ are either detected by the PCDs (at the front surface) or pass through the spaces between the sparsely arranged PCDs and are detected by the tightly packed energy integrating detectors in the X-ray detector 103.

In one implementation, the X-ray source 112, the collimator/filter 114, and the X-ray detector 103 are fixedly connected to a rotational component 110 that is rotatably connected to a gantry, and the PCDs are fixedly connected to a circular component 120 that is fixedly connected to the gantry. The gantry houses many pieces of the CT scanner.

In one implementation, the X-ray source 112, the collimator/filter 114, the X-ray detector 103 are each fixedly connected to a first circular component 110 that is a rotational component rotatably connected to the gantry, and the PCDs are fixedly connected to a second circular component 120 that is fixedly connected to the gantry. The gantry of the CT scanner also includes an open aperture 115 enabling the object OBJ to be placed in a projection plane of the X-rays from the X-ray source. The "projection plane" is a volume wherein X-rays pass from the X-ray source 112 to the detectors including the PCDs and the detector unit 103. The "object space" is the intersection of the projection plane and the open aperture 115 of the gantry. The "image space" includes the union of projection planes corresponding to all projection angles of the X-ray source 112 as the X-ray source 112 rotates around the aperture of the gantry.

A scan is performed when an object OBJ occupies the object space and the X-ray source is rotated through a series of projection angles with the CT scanner acquiring projection data of the X-ray transmission/attenuation through the object OBJ at each projection angle. A scan of the "object projection data" is performed when an image object occupies the object space. A scan of the "calibration projection data" is performed when a calibration object occupies the object space. Calibration objects include air or a known phantom. Calibration projection data is used to correct measurement artifacts in the object projection data, and the corrected object projection data is used to reconstruct an image of the image object.

In general, the photon-counting detectors PCD1 through PCDN each output a photon count for each of a predetermined number of energy bins. In addition to the photon-counting detectors PCD1 through PCDN arranged in the fourth-generation geometry, the implementation shown in FIG. 1B includes a detector unit 103 having energy-integrating detectors arranged in a conventional third-generation geometry. The detector elements in the detector unit 103 can be more densely placed along the detector unit surface than the photon-counting detectors.

In one implementation, the X-ray source 112 and collimator 114 are fixedly placed on a predetermined first circular component 110 in a gantry and diametrically opposed to the detector unit 103 that is also fixedly placed to the circular component 110.

In one implementation, the photon-counting detectors are sparsely placed around the object OBJ in a predetermined geometry such as a circle. For example, the photon-counting detectors PCD1 through PCDN are fixedly placed on a predetermined second circular component 120 in a gantry. In one implementation, the photon-counting detectors PCD1 through PCDN are fixedly placed on the circular component 120 at predetermined equidistant positions. In an alternative implementation, the photon-counting detectors PCD1 through PCDN are fixedly placed on the circular component 120 at predetermined non-equidistant positions. The circular component 120 remains stationary with respect to the object OBJ and does not rotate during the data acquisition.

Both the X-ray source 112, collimator 114 (e.g., a bow tie filter), and the detector unit 103 rotate around the object OBJ while the photon-counting detectors PCD1 through PCDN are stationary with respect to the object OBJ. In one implementation, the X-ray source 112 and collimator 114 are mounted on a first rotating portion 110 such as an annular frame mounted in the gantry so that the X-ray source 112 projects X-ray radiation with a predetermined source fan beam angle $\theta_A$ towards the object OBJ while the X-ray source 112 rotates around the object OBJ outside the sparsely placed photon-counting detectors PCD1 through PCDN. Furthermore, an additional detector unit 103 is mounted on the first rotating portion 110 in the third-generation geometry. The rotating portion 110 mounts the detector unit 103 at a diametrically opposed position from the X-ray source 112 across the object OBJ and rotates outside the stationary circular component 120, on which the photon-counting detectors PCD1 through PCDN are fixed in a predetermined sparse arrangement.

In one implementation, the back surface of each PCD is provided a protective rear cover to shield the PCDs from irradiation from behind as the X-ray source 112 travels outside the first circular path of the sparsely placed photon-counting detectors.

In one implementation, the X-ray source 112 optionally travels a helical path relative to the object OBJ, wherein the table 116 moves the object OBJ linearly in a predetermined direction perpendicular to the rotational plane of the rotating portion 110 as the rotating portion 110 rotates the X-ray source 112 and detector unit 103 in the rotational plane.

The motion of the rotating portion 110 around the object OBJ is controlled by a motion control system. The motion control system can be integrated with a data acquisition system or can separately provide one-way information regarding the angular position of the rotating portion 110 and the linear position of the table 116. The motion control system can include position encoders and feedback to control the position of the rotating portion 110 and the table 116. The motion control system can be an open-loop system, a closed-loop system, or a combination of an open-loop system and a closed-loop system. The motion control system can use linear and rotary encoders to provide feedback related to the position of the rotating portion 110 and the position of the table 116. The motion control system can use actuators to drive the motion of the rotating portion 110 and the motion of the table 116. These positioners and actuators can include: stepper motors, DC motors, worm drives, belt drives, and other actuators known in the art.

In one implementation, a measurement scan is performed by detecting, at the PCDs and detector unit 103, the intensity of X-ray radiation that has propagated from the X-ray source 112 and through the object OBJ before falling incident on the detectors. The X-rays are detected and recorded as the position of the X-ray source 112 is rotated through a series of angles $\Phi = \phi_1, \phi_2, \ldots, \phi_{N\Phi}$. Due to backlash and hysteresis in the actuators, among other factors, the repeatability of the angular position $\Phi$ between scans is imperfect. Angular variations between calibration scans and measurement scans can result in residual measurement artifacts persisting in the calibration-corrected projection data, and those residual measurement artifacts degrade the image quality for images reconstructed from the corrected projection data.

The calibration scans can correct or cancel out many types of measurement artifacts. For example, the absorption values of the calibration scans can be subtracted pixel-by-pixel and frame-by-frame from the absorption values of the object scan. Among these measurement artifacts are the shadowing effect, which results from the back surfaces of PCDs immediately in front of the X-ray source. As the X-ray source position changes, different portions of the object OBJ will be shadowed by these PCDs. If a calibration is used to correct for these shadow regions, a reconstructed image can still be obtained for the entire object OBJ because all shadowed portions of the object OBJ corresponding to one projection angle will be illuminated at other projection angles. However, if there is an offset between the projection angles of the calibration and the object projection data, then the calibration correction (e.g., subtraction) will be imperfect, resulting in residual measurement artifacts (e.g., an offset in the calibration and object projection data shadow regions).

Figure 2:
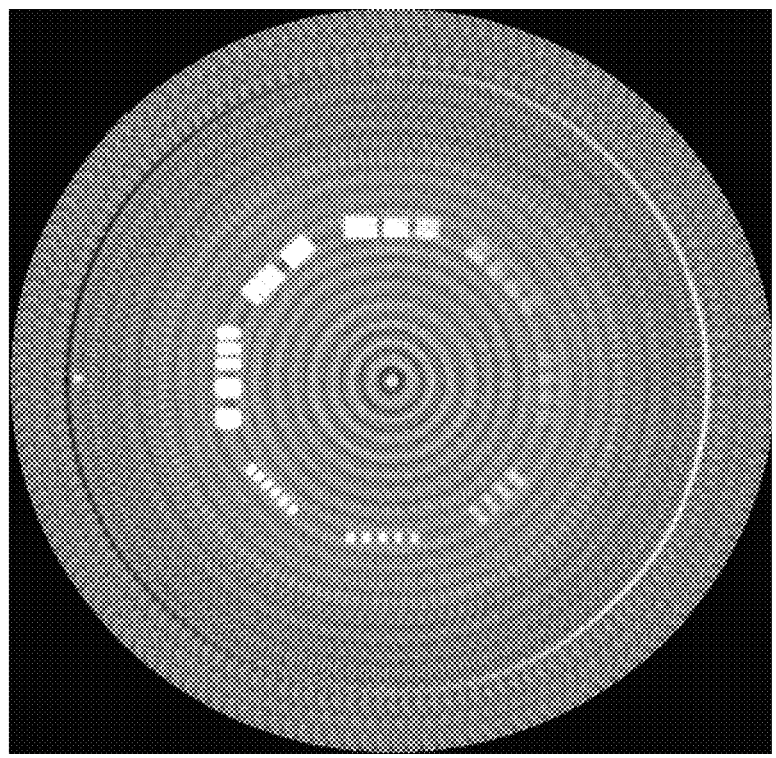
FIG. 2 shows a reconstructed image of an object scan of air, wherein the object scan and a calibration scan have different sub-view angular offsets.

FIG. 2 shows a reconstructed image from object data that has been corrected using calibration data. The object data is taken under identical conditions to the calibration data (i.e., only air is in the object space); therefore, if the calibration correction were perfect the FIG. 2 would show a uniform background of no attenuation. However, because the sub-view angular offset is different between the object data and the calibration data, the calibration correction is imperfect giving rise to the structure shown in FIG. 2 corresponding to attenuation and shadowing by the PCDs.

Figure 6:
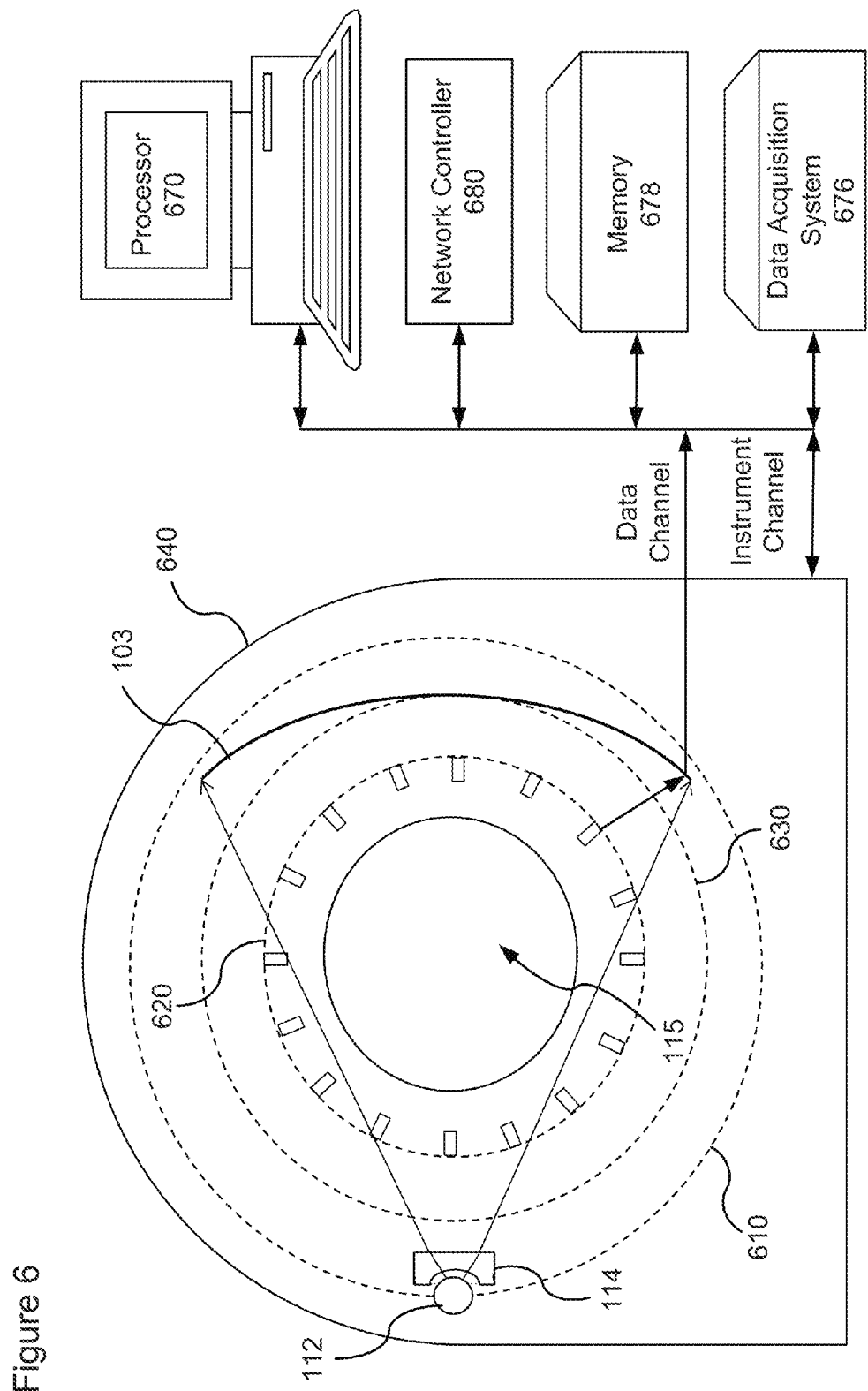
FIG. 6 shows a schematic of an implementation of a CT scanner.

The calibration scans, which are used to measure and correct measurement and detector artifacts, are usually acquired to mimic the real patient scan scenario, including the scan parameters as well as the phantom choices. In some applications, it is important to assure the repeatability of the projection angles of the calibration scan relative to the object/patient scan. For example, in a third- and fourth-generation photon-counting CT scanner, as shown in FIG. 1B and FIG. 6, the PCD ring blocks the X-rays, causing shadows on the detectors. Methods have been proposed to use air or phantom scans to measure the attenuation and beam hardening caused by the PCD. In these calibration scans, it is important to ensure the accuracy and repeatability of the projection angles of the calibration scans. A small sub-angle misalignment (i.e., offset) would cause residual artifacts in the reconstruction, as shown in the FIG. 2.

To mitigate these artifacts, several novel methods are proposed herein to ensure the angular repeatability of the scans. These methods can be used for PCD shadow correction, as well as other calibration tasks that require high view angle accuracy and repeatability. By accurately accounting and correcting for the relative offset angle between calibration and object projection data, the image quality of a reconstructed image can be improved.

Figure 3:
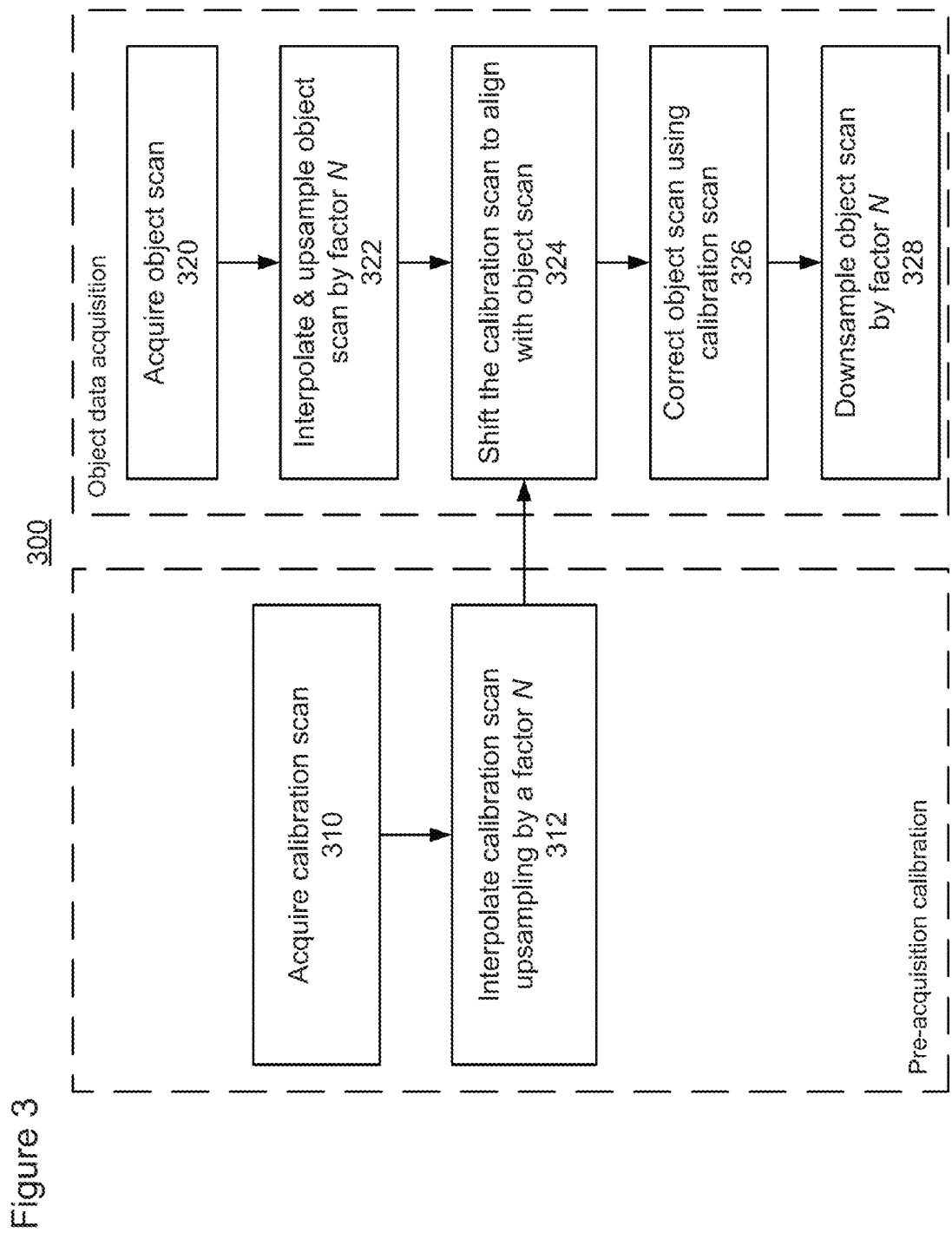
FIG. 3 shows a flow diagram of an implementation of an off-set angle matching method.

FIG. 3 shows a first method 300 to match the offset angle between the actual projection angles of calibration and object data. The term sub-angle refers to deviations from nominal/intended projection angle recorded by the data acquisition system and the motion control system of the CT scanner.

The sub-angles $n\Delta$ are intervals between the measurement angles $\Phi = \phi_1, \phi_2, \ldots, \phi_{N\Phi}$, such that $\Delta = (\phi_{i-1} - \phi_i)/N$. Thus, the region surrounding each measurement angle $\phi_i$, is further subdivided into sub-angles $\phi_i \pm n\Delta$, $n=0, 1, \ldots (N-1)/2$. Each projection data scan will include a sub-view angular offset (i.e., the actual offset angle will fall into one of the bins defined by the sub-angles), where each projection angle $\phi_i$ is offset from its nominal value by an offset angle $n'\Delta$. This offset angle results from imperfections in the motion control system (e.g., backlash in the gears or servo motor). A single sub-view angular offset is assigned to each scan, and the sub-view angular offset is the average angular offset for all of the projections angles in a given scan. Different scans will generally have different sub-view angular offsets, where scans are different if the rotation of the X-ray source 112 is stopped and started between scans.

Where a scan begins with a given sub-view angular offset, generally, that sub-view angular offset continues to be the offset angle throughout the entire scan. Stopping and starting the rotation between scans will generally result in different sub-view angular offsets between scans. Thus, calibration projection data and object projection data that are obtained in separate scans will generally not have identical sub-view angular offsets.

The effectiveness of the calibration correction is limited by how well the sub-view angular offsets match between the calibration data and the object data—a better match resulting in the calibration data better canceling out measurement artifacts (e.g., shadowing by the PCDs) in the object data. Therefore, shifting the sub-view angular offset of the calibration data to match the object data improves the calibration correction and improves the reconstructed image quality.

FIG. 3 shows a method 300 that is a first embodiment of a method for matching the sub-view angular offsets between the calibration data and the object data. The method 300 is divided into two parts: a pre-acquisition calibration part and an object data acquisition part.

The pre-acquisition calibration part of method 300 begins with step 310 in which a calibration scan is performed. The calibration scan includes measuring X-ray projection data at a series of projection angles, wherein the object OBJ is a calibration object (e.g., either air or a predetermined phantom). After step 310, the pre-acquisition calibration part of method 300 proceeds to step 312, wherein the sinogram of the calibration data is interpolated and upsampled by a factor N, wherein the interpolation and upsampling is in the time/angle dimension, as shown in FIG. 1A.

The object data acquisition part of method 300 begins with step 320 by performing an object scan. Like the calibration scan 310, the object scan measures X-ray projection data at a series of projection angles, except in step 320 the scan object OBJ is an image object (e.g., a medical patient) rather than a calibration object. The second step 322 of method 300 is interpolating and upsampling the sinogram of the object data by a factor N, wherein the interpolation and upsampling of the object data is also in the time/angle dimension.

Following step 322, upsampled calibration data and upsampled object data are each used in step 324, and the sub-view angular offset of the upsampled calibration data is adjusted to match the upsampled object data.

In one implementation, the sub-view angular offset of the upsampled calibration data is adjusted by shifting the calibration data sinogram along the time/angle dimension, and the shifted calibration sinogram is compared to the object sinogram. This adjustment of the sub-view angular offset is repeated through numerous iterations to find the best match between the offset angles of the calibration and object data, wherein the "goodness" of the match is determined by a matching function. In one implementation, this iterative search for the best match is an exhaustive search. In one implementation, this iterative search for the best match is a global optimum search method. In one implementation, this iterative search for the best match is a local optimum search method.

The matching function determines the similarity between the upsampled sinogram of the object data and the shifted-upsampled sinogram of the calibration data. In the sinograms the measurement artifacts appear as sine waves having different phases in the object and calibration data. The matching function detects a phase match between the object and calibration sinograms by outputting an extreme value (either a minimum value for a difference measure or a maximum value for an inner product measure). In one implementation, the matching function will provide a distance measure between the object and calibration data (e.g., taking the difference between the object data and the shifted calibration data, and then taking the mean square or a weighted mean square of the difference). In another implementation, the matching function will provide an overlap integral of the object and calibration data (e.g., the inner product between the object data and the shifted calibration data). For the difference measure, a minimum indicates a good match; while, for an inner-product-based match function, a maximum indicates a good match.

As seen in FIG. 1A, near the vertical center line of the sinogram, there is significant overlap between sine waves from the object OBJ, which is near the center of rotation, and measurement artifact sine waves for objects located far from the center of rotation (e.g., PCDs). This overlap can be an obstacle for determining the matching offset angle. For example, saturation effects (e.g., beam hardening) create cross-coupling between superimposed sine waves, making it difficult to determine the phase of the sine wave in the region of overlap. On method to overcome this ambiguity is to use regions of no overlap between sine waves, which is possible when using markers located outside the object space to obtain the matching sub-view angular offset.

Often a CT scanner will include a marker outside the object space but still within the image space. This marker is a constant absorber that is clearly distinguishable in both the calibration data and in the object data. The marker can be a reference. Any easily identifiable/distinguishable measurement artifact can be used as a marker, e.g., the PCDs would be ideal markers. The "object space" is the intersection of the X-ray projection plane and the open aperture 115 of the gantry 640, as shown in FIG. 1B and FIG. 6. The "image space" includes the union of all projection planes corresponding to projection angles of the X-ray source 112 as the X-ray source 112 rotates around the aperture of the gantry 640.

A marker that is outside the object space (e.g., the PCDs shown in FIG. 1B) is advantageous because the sine wave corresponding to the marker has a greater amplitude than sine waves corresponding to objects in the image space. Thus, near its peak and its trough the sine wave of the marker will not overlap with sine waves from the object space. By calculating the matching function in the sinogram regions corresponding to the peaks and troughs of these larger sine waves corresponding to markers outside the object space (i.e., the left- and right-hand regions in the sinogram shown in FIG. 1A), the deleterious effects of nonlinear superposition of sine waves can be avoided.

Having matched the sub-view angular offset of the upsampled calibration data to the object data, the method 300 proceeds to step 326, wherein measurement artifacts are corrected using the phase-corrected-upsampled calibration data. In one implementation, the correction of the object data includes taking the difference between the upsampled object data and the phase-corrected-upsampled calibration data. In one implementation, the correction of the object data includes flagging as unreliable data values of the object data, when the corresponding data values of the phase-corrected-upsampled calibration data exhibit attenuation values above a predetermined threshold (e.g., not using data values for reconstruction when the data values correspond to shadowed detector regions).

Following step 326, method 300 proceeds to step 328, wherein the corrected object data is downsampled by a factor of N, in order to return the corrected object data to the original dimensions of the acquired object data.

In an alternative implementation, the order of the measurement-artifact correction step and the downsampling step are reversed. Thus, in this alternative implementation, step 326 includes downsampling the phase-corrected-upsampled calibration data by a factor of N, and then the object data is corrected using the phase-corrected calibration data. Upsampling before comparing the calibration data to the object data enables finer matching between these two sets of data in order to more exactly determine the sub-view angular offset between the upsampled calibration data and the object data. Downsampling converts the final object data to a resolution matching the original object scan.

Figure 4:
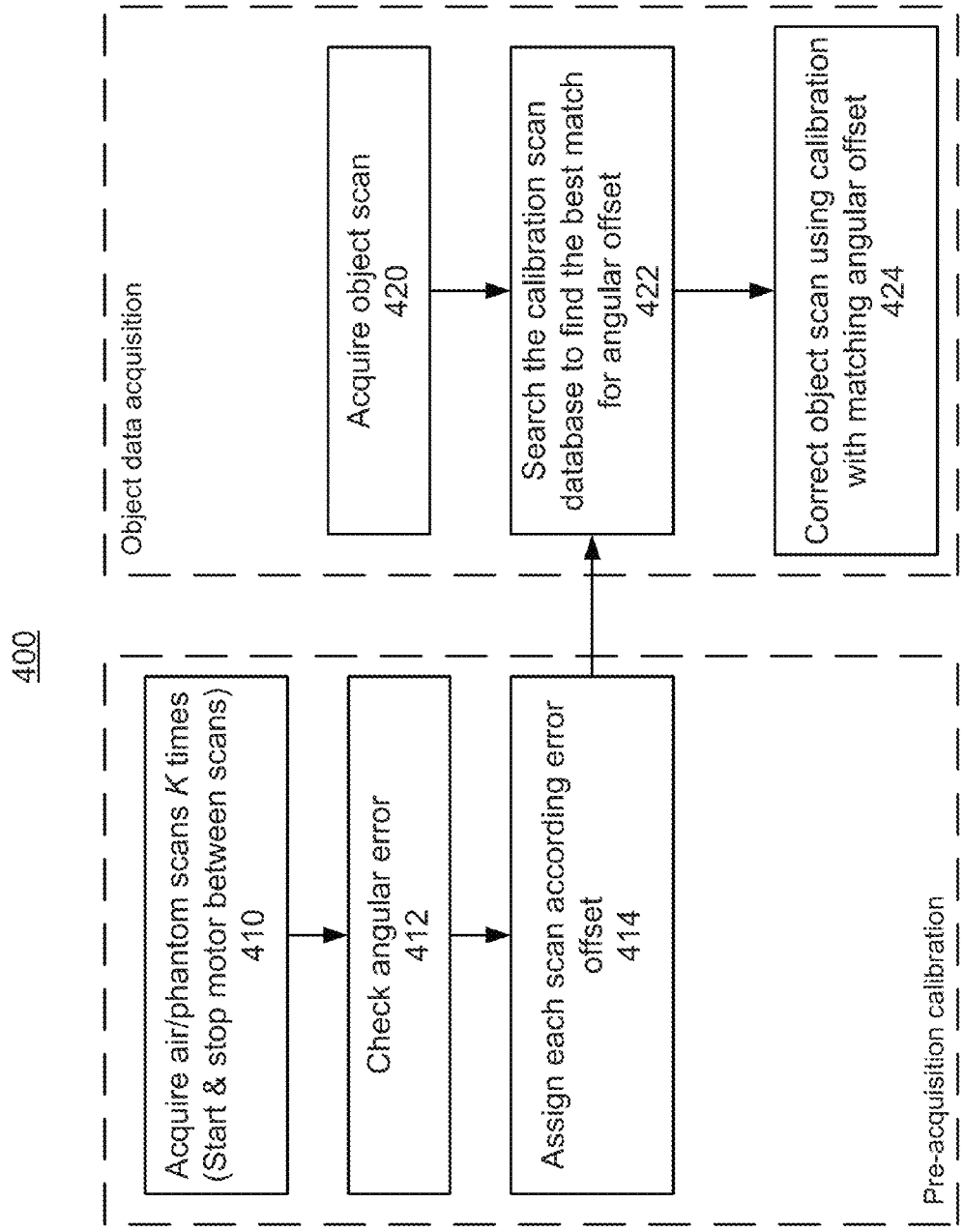
FIG. 4 shows a flow diagram of an implementation of an off-set angle matching method.

FIG. 4 shows a second embodiment of a method for matching the sub-view angular offsets between the calibration data and the object data. The method 400 is divided into two parts: a pre-acquisition calibration part and a patient data acquisitions part.

The pre-acquisition calibration part of method 400 includes three steps: step 410, step 412, and step 414.

Step 410 includes acquiring multiple (K) calibration scans, where each scan includes a complete scan rotation of the CT scanner and the rotation is not continuous between scans (i.e., the rotation is stopped and then started between scans to obtain a unique offset angle for each scan). In one implementation, step 410 includes performing calibration scans to obtain the calibration data. In an alternative implementation, the calibration scans are performed prior to step 410 and the calibration data is stored in a computer readable medium. In this alternative implementation, step 410 includes obtaining the calibration data from the computer readable medium.

Following step 410, step 412 checks the angular offset of each scan. This can be performed by comparing the K calibration scans using the matching function of step 324 to determine the relative offset angles, and assigning the offset angle of one of the calibrations as the zero offset angle.

Following step 412, method 400 proceeds to step 414 where the K calibration scans are each assigned to a sub-view angular offset bin (i.e., $n\Delta$, $n=0, 1, \ldots (N-1)/2$) according to their angular offset relative to the zero offset angle (e.g., the zero offset scan is assigned to the bin $n=0$).

The object data acquisition part of method 400 includes three steps: step 420, step 422, and step 424.

Step 420 includes acquiring an image object scan. The image object (e.g., a medical patient) is located in the object space of the gantry, and the X-ray source is scanned through series of projection angles, measuring the X-ray transmission through the object at each angle.

Following step 420, method 400 proceeds to step 422 in which the object scan is compared to each bin of the calibration scans. In one implementation, a bin average is calculated for each sub-view angular offset bin. The bin average is the average over all calibration scans in a given bin. The comparison between object data and the calibration data uses a matching function to determine the similarity between the object and calibration data. As in step 324 of method 300, in one implementation, the matching function includes a distance measure between the object and calibration data (e.g., taking the difference between the object data and the shifted calibration data, and then taking the mean-square or a weighted mean-square of the difference). In another implementation, the matching function includes an overlap integral of the object and calibration data (e.g., the inner product between the object data and the shifted calibration data). The best match between object data and sub-view angular offset bin is given by the matching function having the optimal value (i.e., a minimum value for a difference measure matching function and a maximum value for an inner product matching function).

Having determined the optimal sub-view angular offset bin, in step 424 the object data is corrected using the calibration data from the sub-view angular offset bin. This correction step is performed similarly to the correction step 326 in method 300, except unlike step 326, there is no downsampling in step 424.

Figure 5:
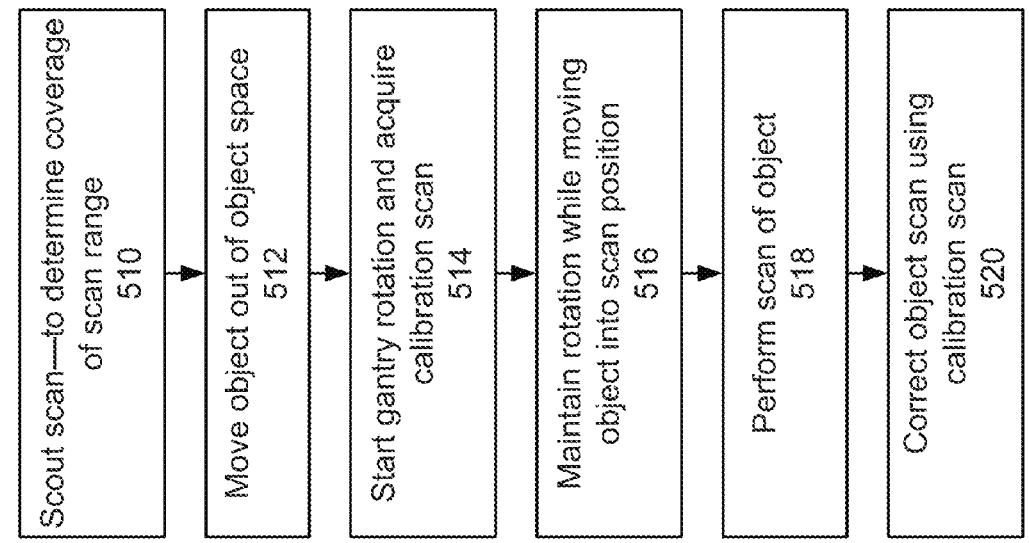
FIG. 5 shows a flow diagram of an implementation of an off-set angle matching method.

FIG. 5 shows a continuous scan method of calibration correction. Because differences in the offset angle between calibration and object data result from stopping and starting the rotation between scans, method 500 uses a continuous scan for both calibration and object data so that the offset angle is the same. This can be achieved by arranging the object OBJ on the table 116 outside of the projection plane and object space. Then after taking a calibration scan with the object OBJ absent from the object space, translating the table 116 to move the object OBJ into the object space while the rotation component 110 is continuously rotating. In order to limit the radiation dosage to a patient, the X-ray source can be prevented from radiating into the object space during this table translation time. With the object OBJ in the object space, the X-ray source radiating into the object space, and the rotation component 110 still continuously rotating, the object data is acquired by recording the X-ray transmissions incident on the detectors. For method 500, the order of the calibration scan and the object scan can be switched provided that the rotation is continuous through both scans.

Method 500 can be subdivided into 6 steps, as illustrated in FIG. 5. The first step 510 is a scout scan to determine the range of the scan.

Next, in step 512, the object is moved out of the object space. This can be achieved by translating the table after the scout scan, such that the object OBJ on the table is no longer in the object space.

Next, the gantry rotation is started in step 514 and the rotation will run continuously until after the object scan is finished in step 518. Also, in step 514 the calibration scan is acquired with the gantry rotation running continuously and the object OBJ absent from the object space.

In step 516, the rotation of the gantry is maintained as the object OBJ is repositioned in the object space. In order to limit the radiation dosage to a patient, the X-ray source can be prevented from radiating into the object space during step 516.

Following step 516, the object scan is performed in step 518 with the gantry rotation running continuously and the object OBJ present in the object space.

Finally, in step 520, similar to steps 326 and 424 of methods 300 and 400 respectively, the object data is corrected using the calibration data.

After the object scan data has been corrected using the aligned calibration data, a CT image can be reconstructed from this projection data using any known CT reconstruction method. For example, the CT reconstruction method can be performed using filtered back projection, iterative image reconstruction methods, or stochastic image reconstruction methods. Further, the CT reconstruction method can be any back-projection method (e.g., filtered back-projection), any iterative reconstruction method (e.g., the algebraic reconstruction technique (ART) method and the total variation minimization regularization methods), any Fourier-transform-based method (e.g., the direct Fourier method), or a statistical method (e.g., the maximum-likelihood expectation-maximization algorithm based methods). Furthermore, if a full scan is not performed, then a short-scan CT reconstruction method can be used, such as the Dreike-Boyd parallel rebinning algorithms, complementary rebinning algorithms, applying suitable weighting function such as the Parker weights to the sinogram, the Katsevich's method, and the Feldkamp method. One of ordinary skill will recognize that many methods of CT reconstruction are possible depending on the type of detectors, source, scan, object, and desired image.

FIG. 6 shows a computed tomography (CT) scanner having both energy-integrating detectors arranged in a third-generation geometry and PCDs arranged in a fourth-generation geometry. Illustrated in FIG. 6 is an implementation for placing the PCDs in a predetermined fourth-generation geometry in combination with a detector unit 103 in a predetermined third-generation geometry in a CT scanner system. The diagram illustrates relative positions among the X-ray source 112, the collimator/filter 114, the X-ray detector 103, and the photon-counting detectors PCD1 through PCDN.

Also shown in FIG. 6 is circuitry and hardware for acquiring, storing, processing, and distributing X-ray projection data. The circuitry and hardware include: a processor 670, a network controller 680, a memory 678, and a data acquisition system 676.

In one alternative implementation, the CT scanner includes PCDs but does not include the energy-integrating detector unit 103.

As the X-ray source 112 and the detector unit 103 rotate around circular paths 610 and 630 respectively, the photon-counting detectors PCDs and the detector unit 103 respectively detect the transmitted X-ray radiation during data acquisition. The photon-counting detectors PCD1 through PCDN intermittently detect the X-ray radiation that has been transmitted and individually output a count value representing a number of photons, for each of the predetermined energy bins. On the other hand, the detector elements in the detector unit 103 continuously detect the X-ray radiation that has been transmitted and output the detected signals as the detector unit 103 rotates. In one implementation, the detector unit 103 has densely placed energy-integrating detectors in predetermined channel and segment directions on the detector unit surface.

In one implementation, the X-ray source 112, the PCDs and the detector unit 103 collectively form three predetermined circular paths that differ in radius. At least one X-ray source 112 rotates along a first circular path 610 while the photon-counting detectors are sparsely placed along a second circular path 620. Further, the detector unit 103 travels along a third circular path 630. The above exemplary embodiment illustrates that the third circular path is the smallest and inside the first and second circular paths.

Although not illustrated, an alternative embodiment optionally changes the relative relation of the first and second circular paths so that the second circular path for the X-ray source 112 is smaller and inside the second circular path 620 of the sparsely placed photon-counting detectors PCD1 through PCDN. The third circular path 630 is always larger and outside of the second circular path 620 in order that the detector unit 103 does not shadow the PCDs from the X-ray source 112.

Furthermore, in another alternative embodiment, the X-ray source 112 also optionally travels on the same third circular path as the detector unit 103, as illustrated in FIG. 1B.

There are other alternative embodiments for placing the photon-counting detectors in a predetermined fourth-generation geometry in combination with the detector unit in a predetermined third-generation geometry in the CT scanner. Several alternative embodiments of the X-ray CT Scanner as described in U.S. Patent Publication No. 2013-0291097, herein incorporated by reference in its entirety.

In one implementation, the X-ray source 112 is optionally a single energy source. In another implementation, the X-ray source 112 is configured to perform a kV-switching function for emitting X-ray radiation at a predetermined high-level energy and at a predetermined low-level energy. In still another alternative embodiment, the X-ray source 112 is a single source emitting a broad spectrum of X-ray energies. In still another embodiment, the X-ray source 112 includes multiple X-ray emitters with each emitter being spatially and spectrally distinct.

The detector unit 103 can use energy integrating detectors such as scintillation elements with photo-multiplier tubes or avalanche photo-diodes to detect the resultant scintillation photons from scintillation events resulting from the X-ray radiation interacting with the scintillator elements. The scintillator elements can be crystalline (e.g., NaI(Tl), CsI (Tl), CsI(Na), CsI(pure), CsF, KI(Tl), LiI(Eu), $BaF_2$, $CaF_2$ (Eu), ZnS(Ag), $CaWO_4$, $CdWO_4$, YAG(Ce), $Y_3Al_5O_{12}$(Ce), GSO, LSO, $LaCl_3$(Ce), $LaBr_3$(Ce), LYSO, BGO, $LaCl_3$ (Ce), $LaBr_3$(Ce), $C_{14}H_{10}$, $C_{14}H_{12}$, and $C_{10}H_8$), an organic liquid (e.g., an organic solvent with a fluor such as p-terphenyl ($C_{18}H_{14}$), PBD ($C_{20}H_{14}N_2O$), butyl PBD ($C_{24}H_{22}N_2O$), or PPO ($C_{15}H_{11}NO$)), a plastic (e.g., a flour suspended in a solid polymer matrix), or other know scintillator.

The PCDs can use a direct X-ray radiation detectors based on semiconductors, such as cadmium telluride (CdTe), cadmium zinc telluride (CZT), silicon (Si), mercuric iodide ($HgI_2$), and gallium arsenide (GaAs). Semiconductor based direct X-ray detectors generally have much faster time response than indirect detectors, such as scintillator detectors. The fast time response of direct detectors enables them to resolve individual X-ray detection events. However, at the high X-ray fluxes typical in clinical X-ray applications some pile-up of detection events will occur. The energy of a detected X-ray is proportional to the signal generated by the direct detector, and the detection events can be organized into energy bins yielding spectrally resolved X-ray data for spectral CT.

The CT scanner also includes a data channel that routes projection measurement results from the photon-counting detectors and the detector unit 103 to a data acquisition system 676, a processor 670, memory 678, network controller 680. The data acquisition system 676 controls the acquisition, digitization, and routing of projection data from the detectors. The data acquisition system 676 also includes radiography control circuitry to control the rotation of the annular rotating frames 610 and 630. In one implementation data acquisition system 676 will also control the movement of the bed 116, the operation of the X-ray source 112, and the operation of the X-ray detectors 103. The data acquisition system 676 can be a centralized system or alternatively it can be a distributed system. In an implementation, the data acquisition system 676 is integrated with the processor 670. The processor 670 performs functions including reconstructing images from the projection data, pre-reconstruction processing of the projection data, and post-reconstruction processing of the image data. The processor 670 also performs the functions and methods (i.e., those methods shown in FIG. 3, FIG. 4, and FIG. 5) of matching the offset angle of calibration data to the offset angle of object data.

The pre-reconstruction processing of the projection data can include correcting for detector calibrations, detector nonlinearities, polar effects, noise balancing, and material decomposition.

Post-reconstruction processing can include filtering and smoothing the image, volume rendering processing, and image difference processing as needed. The image reconstruction process can be performed using filtered back projection, iterative image reconstruction methods, or stochastic image reconstruction methods. Both the processor 670 and the data acquisition system 676 can make use of the memory 676 to store, e.g., projection data, reconstructed images, calibration data and parameters, and computer programs.

The processor 670 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the reconstruction processor may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display. The display can be an LCD display, CRT display, plasma display, OLED, LED or any other display known in the art.

The memory 678 can be a hard disk drive, CD-ROM drive, DVD drive, FLASH drive, RAM, ROM or any other electronic storage known in the art.

The network controller 680, such as an Intel Ethernet PRO network interface card from Intel Corporation of America, can interface between the various parts of the CT scanner. Additionally, the network controller 680 can also interface with an external network. As can be appreciated, the external network can be a public network, such as the Internet, or a private network such as an LAN or WAN network, or any combination thereof and can also include PSTN or ISDN sub-networks. The external network can also be wired, such as an Ethernet network, or can be wireless such as a cellular network including EDGE, 3G and 4G wireless cellular systems. The wireless network can also be WiFi, Bluetooth, or any other wireless form of communication that is known.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
   processing circuitry configured to obtain object projection data and calibration projection data, wherein the object projection data represents an intensity of X-rays transmitted through an image object and detected by X-ray detectors, the object projection data being measured at a first plurality of projection angles relative to the image object, and
   the calibration projection data represents an intensity of X-rays transmitted through a predetermined calibration object and detected by X-ray detectors, the calibration projection data being measured at a second plurality of projection angles relative to the calibration object;
   align the calibration projection data to the object projection data by upsampling, by a factor N, and interpolating a sinogram of the calibration projection data along a time dimension, and
   upsampling, by the factor N, and interpolating a sinogram of the object projection data along the time dimension, wherein the calibration projection data is aligned to have a sub-view angular offset, which is a difference between actual projection angles and nominal projection angles, matching the first plurality of projection angles; and correct the object projection data using the aligned calibration projection data.

2. The apparatus according to claim 1, wherein the predetermined calibration object is one of air and a phantom.

3. The apparatus according to claim 1, wherein the processing circuitry is further configured to align the projection angles of the calibration projection data by shifting the upsampled sinogram of the calibration projection data along the time dimension to match the upsampled sinogram of object projection data.

4. The apparatus according to claim 3, wherein the processing circuitry is further configured to
correct the object projection data by
using the shifted upsampled sinogram of the calibration projection data to correct a measurement artifact in the upsampled sinogram of the object projection data, and
downsampling, by the factor of N, the corrected upsampled sinogram of the object projection data.

5. The apparatus according to claim 3, wherein the processing circuitry is further configured to shift the upsampled sinogram of the calibration projection data using a process for determining the match between sinograms that includes calculating a norm of the difference between the upsampled sinogram of the calibration projection data and the upsampled sinogram of the object projection data.

6. The apparatus according to claim 3, wherein the processing circuitry is further configured to shift the upsampled sinogram of the calibration projection data using a process for determining the match between sinograms that includes calculating an inner product between the upsampled sinogram of the calibration projection data and the upsampled sinogram of the object projection data.

7. The apparatus according to claim 1, further comprising:
a gantry including
an aperture with an object space in the aperture, where the object space is an intersection between the aperture and a projection plane of the X-rays from the X-ray source,
a rotational component provided around the object space that is rotatably connected to a stationary component of the gantry, and
an X-ray source fixedly connected to the rotation component and configured to radiate X-rays into the object space, wherein
the processing circuitry is further configured to
obtain object projection data and calibration projection data by performing at least one scan, wherein each scan includes rotating the X-ray source around the object space, the projection angle of the X-ray source changing according to the position of the X-ray source relative to the object space, and the X-rays being transmitted through the object space and then detected by X-ray detectors opposite the X-ray source.

8. The apparatus according to claim 7, wherein the processing circuitry is further configured to
align the projection angles of the calibration projection data to match the sub-view angular offset of the object projection data using an at least one marker located exterior to the object space, wherein matching between the calibration and object projection data is evaluated using regions of the sinograms corresponding to attenuation signals of the at least one marker located exterior to the object space, but not corresponding to attenuation signals resulting from the object space.

9. The apparatus according to claim 7, wherein the processing circuitry is further configured to
align the projection angles of the calibration projection data to match the sub-view angular offset of the object projection data using a continuous rotation method to acquire both the calibration projection data and the object projection data using one continuous scan, wherein, in performing the continuous rotation method, the processing circuitry is configured to
begin rotation of the X-ray source around the object space,
acquire calibration projection data with the image object absent from the object space and without interrupting the rotation of the X-ray source around the object space,
move the image object into the object space,
acquire object projection data with the image object in the object space and without interrupting the rotation of the X-ray source around the object space, and
end rotation of the X-ray source around the object space.

10. The apparatus according to claim 7, wherein the processing circuitry is further configured to
align the projection angles of the calibration projection data to match the sub-view angular offset of the object projection data using a binning method to arrange a plurality of calibration scans in a plurality of sub-view angular offset bins, wherein, in performing the binning method, the processing circuitry is configured to
obtain calibration projection data of the plurality of calibration scans;
arrange the plurality of calibration scans in the plurality of sub-view angular offset bins according to the sub-view angular offset each calibration scan, and
select one of the plurality of sub-view angular offset bins to match the sub-view angular offset of the object projection data.

11. The apparatus according to claim 10, wherein the processing circuitry is further configured to select one of the plurality of sub-view angular offset bins that matches the sub-view angular offset of the object projection data using a matching method to determine an optimized match using a matching method that is one of a norm-difference method and an inner-product method.

12. A method, comprising:
obtaining object projection data and calibration projection data, wherein the object projection data represents an intensity of X-rays transmitted through an image object and detected by X-ray detectors, the object projection data being measured at a first plurality of projection angles relative to the image object, and
the calibration projection data represents an intensity of X-rays transmitted through a predetermined calibration object and detected by X-ray detectors, the object projection data being measured at a second plurality of projection angles relative to the calibration object;
aligning the calibration projection data to the object projection data by upsampling, by a factor N, and interpolating a sinogram of the calibration projection data along a time dimension, and
upsampling, by the factor N, and interpolating a sinogram of the object projection data along the time dimension, wherein
the calibration projection data is aligned to have a sub-view angular offset, which is a difference between actual projection angles and nominal projection angles, matching the first plurality of projection angles; and correcting the object projection data using the aligned calibration projection data.

13. The method according to claim 12, wherein the step of aligning the projection angles further comprises:

shifting the upsampled sinogram of the calibration projection data along the time dimension to match the upsampled sinogram of object projection data.

14. The method according to claim 13, wherein the step of correcting the object projection data further comprises:

correcting a measurement artifact in the upsampled sinogram of the object projection data using use the shifted upsampled sinogram of the calibration projection data; and downsampling, by the factor of N, the corrected upsampled sinogram of the object projection data.

15. The method according to claim 12, further comprising:

acquiring object projection data and calibration projection data using a gantry including an aperture with an object space in the aperture, wherein the object space is an intersection between the aperture and a projection plane of the X-rays from the X-ray source, a rotational component provided around the object space that is rotatably connected to a stationary component of the gantry, and an X-ray source fixedly connected to the rotation component and configured to radiate X-rays into the object space, wherein the step of acquiring object projection data and calibration projection data includes performing an at least one scan, the at least one scan including rotating the X-ray source around the object space, the projection angle of the X-ray source changing according to the position of the X-ray source relative to the object space, and the X-rays being transmitted through the object space and then detected by X-ray detectors opposite the X-ray source.

16. The method according to claim 15, wherein the step of obtaining object projection data and calibration projection data further comprises continuously rotating the rotation component and using one continuous scan configured to acquire both the object projection data and the calibration projection data, wherein a first portion of the scan acquires the calibration projection data when the image object is out of the object space, and a second portion of the scan acquires the object projection data when the image object is in the object space.

17. The method according to claim 15, wherein the step of aligning the projection angles further comprises using a binning method, wherein the calibration projection data includes a plurality of calibration scans where the rotation of the rotation component is stopped and started before each of the plurality of calibration scans, the plurality of calibration scans are arranged in a plurality of sub-view angular offset bins according to the sub-view angular offset of each of the plurality of calibration scans, and the step of correcting the object projection data comprises using the calibration projection data from the bin of the plurality of sub-view angular offset bins having a sub-view angular offset matching the sub-view angular offset of the object projection data.

18. The method according to claim 17, wherein the step of aligning the projection angles further comprises using one of a norm-difference method and an inner-product method to determine which of the plurality of sub-view angular offset bins matches the sub-view angular offset of the object projection data.

19. A non-transitory computer-readable medium storing executable instructions, wherein the instructions, when executed by processing circuitry, cause the processing circuitry to perform the method according to claim 12.

20. The method according to claim 12, wherein the obtaining of the calibration projection data includes that the predetermined calibration object is one of air and a phantom.

* * * * *